United States Patent [19]

Keith

[11] Patent Number: 5,085,982

[45] Date of Patent: Feb. 4, 1992

[54] METHOD OF DETECTING SPECIFIC SUBSTANCES BY SELECTIVE GROWTH OF LIVING CELLS

[75] Inventor: Douglas H. Keith, Monrovia, Calif.

[73] Assignee: City of Hope, Duarte, Calif.

[21] Appl. No.: 873,504

[22] Filed: Jun. 12, 1986

[51] Int. Cl.⁵ .................. C12Q 1/68; C12Q 1/70; G01N 33/543

[52] U.S. Cl. .................. 435/5; 435/6; 435/7.1; 435/7.5; 435/29; 436/501; 436/518

[58] Field of Search .......... 435/7, 29, 948, 5, 6, 435/7, 7.1, 7.5; 436/501, 518

[56] References Cited

U.S. PATENT DOCUMENTS

| | | | |
|---|---|---|---|
| 4,104,126 | 8/1978 | Young | 435/5 |
| 4,321,365 | 3/1982 | Wu et al. | 435/172.3 |
| 4,746,604 | 5/1988 | Mowshowitz | 436/579 |

OTHER PUBLICATIONS

Hamada et al., Gene, 24, 245-253, 1983.

*Primary Examiner*—David A. Saunders
*Attorney, Agent, or Firm*—Edward S. Irons

[57] ABSTRACT

The invented method utilizes a signal amplification system comprising living cells which are specifically provided with the ability to survive, reproduce and be detected in the event that a target molecule is present. The method comprises first the step of binding a target molecule to a substratum. In the second step a phagemid is prepared which is capable of transfecting a cell enabling such transfected cell to produce a signal, such as color or light. The phagemid is then provided with a means for binding to a probe, thus forming a phagemid complex.

The probe may also be provided with a means of binding to the phagemid complex. This modified probe is then hybridized with the target molecules bound to the substratum. Thereafter, the phagemid complex is hybridized with the modified probe and specific binding occurs between the phagemid complex and the modified probe thus forming a substrutum-target-probe phagemid complex. As a next step, lysogenic bacterial cells which are infectable by the particular phagemid being used are added to the system in an environment which favors transfection of the phagemid nucleic acid into the bacteria. The growth medium is constituted so that only transfected bacteria survive and are capable of reproducing. The phagemid also enable the bacteria to produce a signal such light or color. Only the transfected bacterial cells containing the plasmid gene for producing the signal will be detectable.

6 Claims, 1 Drawing Sheet

FIG. IA
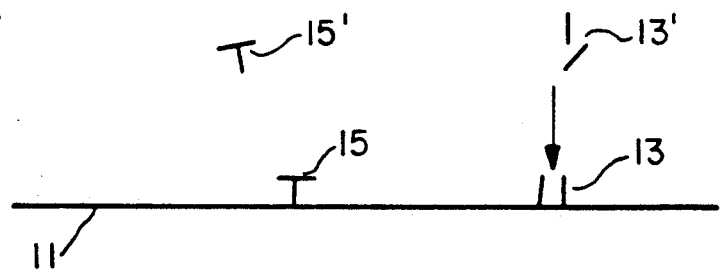
FIG. IB
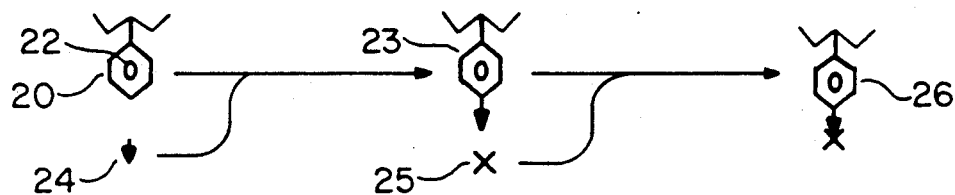
FIG. IC
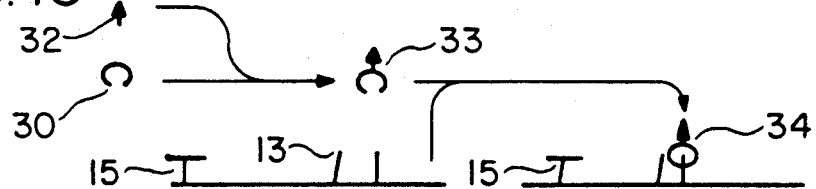
FIG. ID
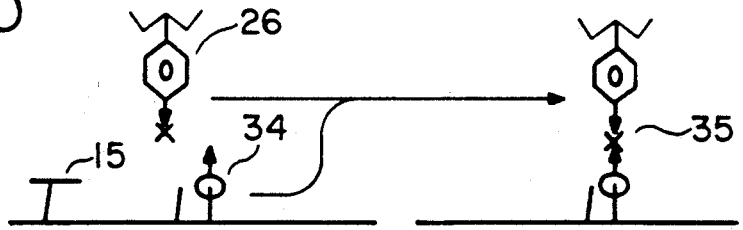
FIG. IE
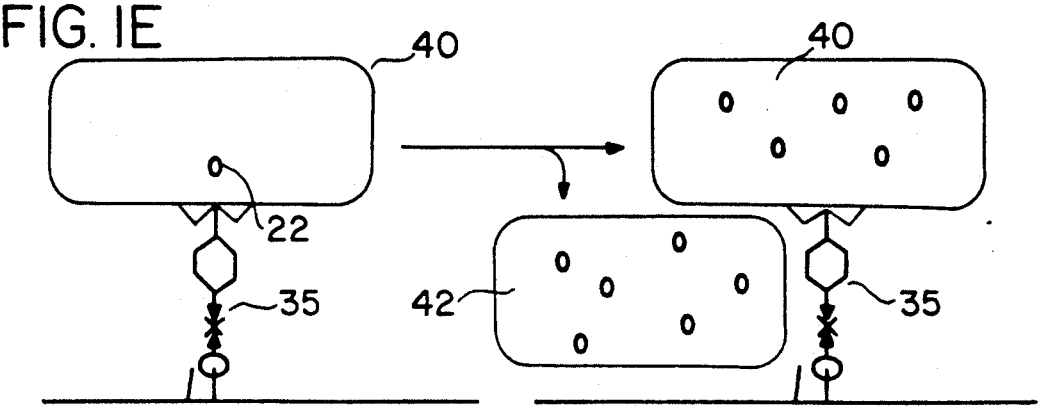

METHOD OF DETECTING SPECIFIC SUBSTANCES BY SELECTIVE GROWTH OF LIVING CELLS

BACKGROUND OF THE INVENTION

1. Field of the Invention

This invention relates generally to the field of biotechnology, and, more specifically, to a process for detecting specific molecules in an in vitro system by the detection of a signal produced by a living cell or selectively grown cells.

2. Prior Art

A number of prior methods have been developed and used extensively for the detection of specific molecules, such as DNA, RNA, protein, peptides, carbohydrates, fats, minerals, various organic and inorganic molecules, including complexes of the same. For example, in the area of basic biological research, the identification of specific chains of DNA and RNA is important in the determination of the genetic makeup of cells, and the isolation and purification of nucleic acids for recombinant DNA technology.

In the field of medical diagnostic testing and research the diagnosis of certain genetic diseases requires the identification of specific DNA segments. Some of these assays use DNA restriction-fragment-length-polymorphisms (RFLP) as tools for diagnosis of genetically linked diseases in which DNA of affected individuals is analyzed using Southern blotting to reveal a particular restriction fragment length cf DNA in close genetic linkage to a gene defect.

As other examples, the detection of cancer, the evaluation of the progress of cancer treatment drugs on such cancers, and the characterization of tumors is dependent on the ability to detect and measure the level of various blood factors, hormones, drugs, proteins and other biological molecules in the blood and other body fluids and tissues. On therapeutic drug monitoring, See *Human Pathol,* 15:404–411 (1984); on assays for drugs, hormones, proteins and antigens, including viral and bacterial antigens, see *Human Pathol.* 15, 112-116 (1984); on diagnosis of infectious disease, see *Ann. N.Y. Acad Sci* 428:223-229 (1984).

In the prior art, there are essentially three types of systems for the detection of specific molecules. The first method, and the one that has been used most extensively in recent years, involves the use of radioactive molecules (radio immune assays or RIAs; Southern, Northern and Western blots etc.) A second method, which in general is less sensitive, is the use of enzymatic reactions. The third method, which is generally least effective because of its relative insensitivity and requirement for very detailed technical work, is the use of physical detection methods, such as infra-red spectrum, NMR spectrum, UV absoption, fluorescence and the like.

With respect to radioactive probes, it is well-known that the more sensitive the probe is, the more radioactive it must be. Thus, highly radioactive molecules, such as those containing iodine-125 or phosphorous-32 isotopes decay relatively rapidly so that the radioactive decay can destroy the probe designated to identify the target molecule. Furthermore, in view of the rapid radioactive decay, these radioactive probes have a short shelf life. Moreover, they are hazardous to work with and difficult to dispose of, as a result of the innate problems involved with a dangerous radioactive material.

In enzymatic systems, an enzyme is chemically coupled to a molecule that is capable of specifically binding with a target molecule which is to be detected. The enzyme thereafter is induced to produce a signal by acting on a substrate to convert it into a detectable colored molecule, or result in the production of light of a particular wave length, and the signal is detected by known means.

Unfortunately in both the radioactive and enzymatic signal systems, one probe is capable of producing only a limited signal. That is, the molecule (i.e. the probe) that is capable of binding to the target molecule can only attach to or react with a single or a very small number of signal producers. If the signal is a radioactive probe, such as phosphorous-32, only a limited number of phosphorous-32 molecules can be bound to the probe. Each individual phosphorous-32 molecule can only emit a single signal upon disintegration; that is, each phosphorous-32 molecules can only decay once in a manner that will be detected by a radioactive counter, or by autoradiography. Similarly, with respect to an enzymatic signal system, there is a limited amount of substrate with which a single enzyme molecule coupled to a probe may catalyze a reaction within a specified time period to thereby produce a signal indicating detection of the target molecule. Another problem with this system is that the product of the enzymatic reaction is often designed to be relatively insoluble in order to limit diffusion of the signal, thus limiting substrate access to the enzyme.

3. Definitions

The following terms will be used herein and are defined as follows to facilitate understanding of this patent. The definitions provided are not intended to limit in any way the scope of this patent or restrict the definitions to be narrower than is understood in the field.

Amplify—to increase the level of a signal denoting the presence of a target molecule with the intention of making the signal detectable. Amplification is particularly useful when the target molecule is only available in very low concentrations.

Lysogenic bacteria—Bacteria which contain a phage genome incorported within the bacterial genome. The incorporated phage genome produces a repressor molecule which inactivates its own gene systems as well as inactivating similar phages (upon which the repressor has a proper binding site) which enter that bacteria.

Phage (bacteriophage)—a virus comprising a protein coat and nucleic acids. The phage is capable of attaching to a bacterial cell and injecting its DNA (or RNA) into the cell. Thereafter, the phage may use the cell's synthesis abilities to reproduce copies of the phage's genome and protein coat, which combine and subsequently are extruded or burst out of a cell, and which, in turn, are then able to infect other cells. Alternatively the phage may innocuously replicate its DNA within its host bacterias' DNA and latently infect the bacterial cell's progeny (in the case of lysogenic bacteria).

Phagemid—a combination of a phage and a plasmid. A phagemid can infect a bacteria like a phage, but in a lysogenic bacteria can only replicate by using the plasmid origin of replication, in which case the phage behaves like a plasmid with essentially all of the phage genes turned off, so that only the plasmid genes are expressed.

Plasmid—a circular piece of DNA which can replicate and maintain an independent existence in bacterial cytoplasm, separate from the bacterial chromosome.

Probe—a molecule that can bind, by means of ionic, steric or other known forms of interaction, to another specific or "target" molecule. Antigen-antibody, enzyme-substrate, DNA and RNA complements are examples of possible probes binding to specific molecules.

Replication—the duplication of a DNA molecule to make a copy of the same. Replication occurs when a cell divides so that both daughter cells have the same DNA content.

Signal—any message which is intended to be detected, thereby indicating the presence of a target molecule.

Southern Blotting—method of detecting the existence of specific DNA fragments. The target DNA fragments are bound to a substratum and the probe DNA or RNA fragments are radioactively labelled and then hybridized to the bound fragments. The successfully hybridized fragments (indicating a match between target and probe) are then detected, generally by autoradiography. See *Meinkoth and Wahl*, "Hybridization of Nucleic Acids Immobilized on Solid Supports, Anal. BioChem. 138, 267-284 (1984); *Wahl et al*, "Efficient transfer of large DNA fragments from agarose gels to diazbenzylomethyl-paper and rapid hybridization by using dextran sulfate," Proc. Nat. Acad. Sci. U.S.A., 76:3683-3687 (Aug. 1979); and *Southern*, "Detection of Specific Sequences Among DNA Fragments Separated by Gel Electrophoresis," J. Mol. Bio. 98: 503-517 (1975).

Substratum—any immobilized material or surface which immobilizes the target.

Tag—any chemical linkage between two molecules.

Target or Target Molecule—any molecule which is intended to be detected.

Transfection—the act of a virus (phage) injecting its DNA (or RNA) into a host cell.

SUMMARY OF THE INVENTION

The present invention comprises a method for the detection and quantification of specific molecules, such as, specific DNA, RNA and segments thereof, proteins, peptides, lipoproteins, carbohydrates, fats, minerals and other organic and inorganic molecules, and complexes of the same. The invented method utilizes a signal amplification system comprising living cells which are specifically provided with the ability to survive, reproduce and be detected in the event that a target molecule is present.

The method comprises first the step of binding a target molecule to a substratum. In the second step a phagemid is prepared which is capable of transfecting a cell enabling such transfected cell to produce a signal, such as color or light. The phagemid may also contain a gene which permits transfected bacteria to survive in a particular environment, thereby limiting background noise. For example, the phagemid may contain a gene for antibiotic resistance, so that only transfected bacteria may survive in a growth media containing the antibiotic. The phagemid is then provided with a means for binding to a probe.

One principal example of such a binding system is biotin which is known to bind specifically to streptavidin ("avidin"). Biotin may be bound to the phagemid, and avidin is then bound to the biotin-phagemid complex. The probe is also tagged with biotin molecules. The biotin tagged probe is then hybridized with the target molecules bound to the substratum. Probe-target interactions can be selectively retained so that the biotin tagged probe is primarily coupled to target molecules. Thereafter, the avidin-biotin-phagemid complex is hybridized with the biotin tagged probe and specific binding occurs between the avidin on the avidin-biotin-phagemid complex and the biotin on the biotin probe thus forming a substratum-target-probe-biotin-avidin-biotin-phagemid complex. (The avidin can bind up to four biotin molecules.) The non-specifically bound phagemids are then removed.

As a next step, lysogenic bacterial cells which are infectable by the particular phagemid being used are added to the system in an environment which favors transfection of the phagemid nucleic acid into the bacteria. The growth media is preferably constituted so that only transfected bacteria survive and are capable of reproducing. The phagemid can also enable the bacteria to produce a signal such as light or color. A number of such signal systems are known in the art. Only the transfected bacterial cells containing the plagemid gene(s) for producing the signal will be detectable. This occurs because the phagemid gene(s) is, or can be induced to be, expressed which results in a particular signal. The bacterial cells are selectively grown with each surviving progeny containing the gene(s) for signal production. This signal thus produced is amplified to a readable level. If no target molecules are present on the substratum, the biotin tagged probe which specifically binds only to the target, will not be found on the substratum, and consequently there will be no binding site for the avidin tagged phagemid. Without the presence of phagemid on the substratum, the bacterial cells added thereon will not be transfected with the signal producing gene and no signal will be produced.

Other variations of the invented system will be discussed below. As will become clear, the invented system is not limited to the specific embodiments described herein. It will be appreciated by one skilled in the art that a number of variations embodying the invented process of utilizing living cells to amplify a signal indicating the detection of a target molecule come within the spirit and scope of the present invention.

BRIEF DESCRIPTION OF THE DRAWINGS

FIG. 1 illustrates the steps of the present invention in schematic form.

FIG. 1A illustrates the binding of target molecules onto a substratum.

FIG. 1B illustrates the preparation of a biotin-phagemid, complex and then an avidin-biotin-phagemid complex.

FIG. 1C illustrates the binding of a biotin molecule to a probe, and the binding of a biotin-probe complex to the target molecule.

FIG. 1D illustrates the binding of the biotin-probe-target-substratum complex to the avidin-biotin-phagemid complex FIG. 1E illustrates the addition of a bacterial cell to the system, the transfection of the phagemid genome into the bacterial cell, and the subsequent replication of the phagemid genome in the bacterial cell and its progeny.

DETAILED DESCRIPTION

The present invention comprises a method for detecting virtually any type of target molecule and may be understood in a broad sense with reference to the drawings. FIG. 1 illustrates one embodiment of the invented system utilizing a biotin-avidin binding system. As explained below, other binding systems for binding the constructed phagemid to the probe may be used as well. A direct probe-spore amplification system will also be described.

Substratum

The substratum is a surface upon or within which a target molecule will be contained or bound. In general, there are three catagories of substratum that may be employed:

(1) porous flat substratum membranes and papers, including covalent binding paper, (such as DBM paper, cyanuric chloride activated paper, and APT paper) nylon membranes, other membranes made from synthetics (expecially polyester, rayon, orlon, dacron, etc.), natural fibers and modified natural fibers, such as cellulose, nitrocellulose and 541 paper by Millipore);

(2) gels in which the target molecules are bound, such as dried agarose gels, polyacrylamide gels, starch gels (See Anal. Biochem. 131:365–372, 1983); and (3) solid surfaces upon which the target molecule is bound either directly or by other intermediary molecules. One category of solid surfaces commonly used are plastics including polyethylene, polycarbonate, polystyrene, polypropylene with and without chemical modification of surface-charged groups on the plastic. Refs: (ELISA) Anal. Biochem. 105:375–382, 1980; Biotech. Lett. 2:429–434, 1980. Glass could also be used.

Usually the third class of substratum is used with microtiter-type assays. Small wells are individually assayed for the presence or absence and quantity of a signal designating the presence quantity of a target molecule. Numerous radioimmune assays, ELISA (enzyme linked immunosorbent assays), and EIA (enzyme-immuno assays) utilize this technology. Often an antibody specific to the target molecules, or an antigen specific for a target antibody is bound to (or dried on) the plastic substratum. The target molecules that are bound will usually be proteins and/or nucleic acids. The proteins may have associated fats or carbohydrate moieties.

Binding Target To Substratum

As shown in FIG. 1A, a relatively "flat substratum," is provided, such as nitrocellulose membrane, for binding the target molecule non-specifically. Free target molecules 13' are bound to the substratum 11 to form bound target 13. Other free non-target molecules 15' may also be bound to the substratum 11 to form bound non-target 15.

Phagemids

In FIG. 1B, a phagemid 20 containing a specifically constructed phage-plasmid hybrid DNA 22 having a gene coding for a specific signal is provided. The production and characterization of phagemids has been described in the literature under various names, including phage-plasmid hybrid or plasmid phage hybrid (Gene 24:245–251, 1983), plasmidophages (Biochimie 60:183–187, 1978), phasmids (Gene 17:27–44, 1982; Gene 22:75–83), and phagemid, (Gene 28:29–35, 1984). Plasmids which contain the signal sequences for phage packaging, although requiring a helper phage could still be used for the purposes herein described. All of the foregoing constructs are contemplated as being contained within the definition of phagemid as that is used herein.

The specific signals which may be selected have also been described in the literature, such as the luciferase system producing light (CELL 32:773–781 (1983) and B-galactosidase, producing blue color, (Davies & Jacob. J. Mol. Biol. 36:413, 1968). Antibiotic resistance can also be incorporated into the phagemid which allows the survival and selective growth of previously antibiotic sensitive bacterial strains as another marker.

Specific phagemids have been constructed which permit an infected bacteria to grow in the presence of ampicillin and enable the bacteria to produce light (Phagemid λ JE) or provide ampicillin resistance and produce a blue color (Phagemid λ YAB) when the bacteria are grown in media containing X-gal (5-Br-4-Cl-3-indolyl-B-D-galactopyranoside and IPTG (Isopropyl-B-D-Thio-galacto-pyranoside, an inducer of the Lactose operon). In addition, some of the pigment-producing capabilities of various bacteria may be employed by cloning the relevant genes into a phagemid. Yellows, reds, greens, and blues may be produced in this way without the necessity of adding an expensive chemical, such as X-gal. These pigments are also advantageous because they are maintained within a cell, rather than being diffused into the media. As another method for producing a color signal there are some stains that, when included in a bacterial medium, are take up in bacteria. Such color would be readily visible as a colored bacterial colony on a white substratum. (Ref.: Hopwood, D. A. "General review of indicator plate methods." Methods in Microbiology, Vol. 3A, p. 363. New York, Academic Press, 1970.)

Another possible signal system involves enabling bacterial or other living cells to produce enzymes that result in the synthesis of molecules that are particularly fluorescent or that have a tendency to bind fluorescent molecules or atoms.

Other phagemids can be produced by persons of ordinary skill in the art, with any of a number of specially selected genes for signals. Phagemids are a recombinant construct, and are generally unavailable commercially. Some references to phagemid construction include:

Gene 24:245–253, 1983.
Gene 28:29–35, 1984.
Biochimie 60:183–187, 1978.
Gene 22:75–83, 1983.
Gene 17:27–44, 1982.

Biotinylating The Phage

The phagemid 20 was bound to a biotin molecule 24 to form a phagemid-biotin complex 23 by the following method, which has been described in the art (Nucleic Acids Research 13:45–56 (1985)), (Nucleic Acid Research 13:745 (1985)) and (PNAS, USA 78:6633–7 (1981)).

Coupling To Avidin

The phagemid-biotin complex 23 is then coupled to avidin 25 using the method described below to form a phagemid-biotin-avidin complex 26.

Probe Biotin Complex

FIG. 1C illustrates the preparation of a probe which, is any molecule which specifically binds the target 13 molecule. The probe can be any segment of DNA, an antibody (or antigen), an enzyme, or the like depending upon the target. The probe 30 is bound to biotin 32 to form a probe-biotin complex 33. This may be done by incorporating a nucleotide into the DNA or RNA, such nucleotide having a biotin molecule attached, or it can be added later such as by photobiotin. The probe is then ready for application to the substrate-target complex, described below.

The probe-biotin complex 33 is then hybridize with the target 13 under the following conditions to form a target-probe-biotin complex 34. Of course, the specific conditions will depend on the nature of the probe and target. Unbound probe-biotin complex 33 is then washed away. As shown, no probe-biotin complex is bound to the non-target molecules 15.

In FIG. 1D, the phagemid-biotin-avidin complex 26 is hybridized to the target-probe-biotin complex 34 to form a target-probe-biotin-avidin-biotin-phagemid complex 35 on the substratum 11 and all unbound material is washed away.

In FIG. 1E, bacterial cells are added, and the phagemid 20 transfects its plasmid 22 into the bacterial cell 40. A number of copies of the plasmid 22 may be produced by the bacterial cell, and each copy replicates. Upon division of the bacterial cell 40, the daughter cells 42 and all future progeny contain the plasmid 22. The signal produced by these cell(s) is a product of the proteins coded for by the genes on those plasmids.

General requirements for λ YAB recipients

Bacteria should be a lambda lysogen and be lac⁻ (missing all or part of the B-galactosidase operon). Rec A, B, and C mutations help limit instability of certain sequences, but only certain phages can grow in recA⁻ strains. The Charon 35 derivative (phagemids) can grow on recA⁻strains. Only the lysogenic condition and lac⁻ (a deletion in the lactose operon Z gene) are necessary for λ YAB, and no particular mutation is necessary for λ JE, just a transfectable lambda lysogen strain compatible with PBR322 like replication.

Two specific bacterial strains useful for the present invention are (JM3 λ Cl), and (JM109 λ Cl) which have mutations in the B-galactosidase gene and are lysogenic for lamda phage.

The bacteria are permitted to multiply until a desired intensity of signal is obtained. The signal can be induced by any of a number of methods known in the art, depending upon the signal system employed. The strength of the signal is a direct function of the number of transfected cells and their progeny which are capable of producing a signal.

Other types of cells may be used, both procaryote and eucaryote. Different types of viruses, phages, phagemids, prions, resistance genes, growth complementing genes, or signal producing genes and different replicons may also be used.

Types Of Probes (Examples)

Probes are molecules that will specifically complex with a target molecule. Examples of a probe molecule are: antibodies complexing to any of a number of haptens (small molecules) or recognizing binding sites on proteins, carbohydrates, peptides, organic substances and other molecules, cofactors—(specifically complexing with proteins requiring cofactors), other tight binding components such as biotin (complexing to avidin) or avidin (complexing to biotin), either of which can be attached to or be a primary probe, RNA's (binding specifically to RNA or DNA target molecules), DNA's (binding specifically to RNA or DNA target molecules), enzymes binding to specific components such as (substrates, products, or molecules mimicking these), substrates or products and mimicking molecules (binding to enzymes), DNA sequence specific proteins (binding specific DNA), RNA sequence specific proteins (binding specific RNA) and specific RNA or DNA molecules binding to specific proteins. These are some of the examples of probe-target combinations.

Other Types Of Binding Between Probe And Amplification System

1. Phagemid may be bound to an antiphage head antibody from a species X, antibody against probe derived from species X, Coupling between these antibodies bringing the whole complex together may be:
   a. Anti-antibody directed against the conserved portion of an antibody derived from species Y.
   b. Avidin coupled either chemically or by biotin to either antibody. The other antibody has its complement, e.g., allows biotin-avidin coupling of antiphage head antibodies and antiprobe antibodies.
   c. Fusion protein antibody. Antibodies to phage head and probe directly coupled.

2. Antibodies to phage head linked to antibody to probe linked by other high-affinity components bound to these antibody components.

3. Phagemid bound by antiphage head antibody with coupled avidin (or biotin-avidin complex) or other high-affinity binders, so that the avidin on the complex binds the biotin on the probe.

4. Avidin chemically complexed to phagemid or spore, which then will bind to biotinylated probe.

5. Avidin being expressed as a fusion protein on the surface of a phage or spore so that it will bind to biotinylated probe. Note: Streptavidin has been cloned.

6. Probe being complexed to avidin (more applicable when probe is a protein or peptide) so that the biotinylated phage phagemid or spore can complete the complex.

7. A fusion protein containing a high-affinity binding site for the probe, such as a lactose repressor protein fused to the phage head protein, which will bind lactose operator sequence of a partially double-stranded DNA probe.

8. Antibiotinylated probe (or antiavidin, or antiavidin biotinylated probe) antibody used in conjunction with some of the coupling mentioned in (1) can be used in conjunction with a biotinylated or avidin linked DNA, RNA or protein probe.

9. One can also use a modified probe, in the form of alkylated DNA, butyrated DNA, in conjunction with antibodies directed against that modified DNA and the modalities mentioned in (1).

10. In addition, many other chemical or enzymatic methods exist to modify DNA RNA or proteins so that they can be recognized by antibodies or bound with some component that binds tightly to that modified probe.

References

1. Covalent linkage of substance to DNA-probe. Proc. Natl. Acad. Sci. USA 81:3297–3301, 1984.
2. Incorporation of nucleic acid base analogs into DNA (to use as probes.) Nucl. Acids. Res. 13:8665–8683, 1985.
3. An SS binding protein complexed to SS DNA probe, to which biotin and subsequent linking and amplifying technologies could be applied. Nucl. Acids. Res. 13:2789–2801, 1985.
4. Modification of DNA (probe) by N-acetoxy-2-actylaminofluorene. Nature 317:175–177, 1985.
5. Example of chemical cross-linking by thiolating reagent Anal. Biochem 148:199–206, 1985.

6. Biotinylated DNA. Nucl. Acids Res. 13:8083-8091, 1985.
7. Thiol-specific biotinylating reagent. Anal. Biochem. 149:529-536, 1985.
8. Chemically binding biotin to DNA. Nucl. Acids Res. 13:1529-1541, 1985.
9. Synthesis of DNA with free sulfhydryl group and attachment of couplers, etc. Nuc. Acids Res. 13:4485, 1985.
10. Enzymatic synthesis of biotin DNA. Proc. Natl. Acad. Sci. USA 78:6633-6637, 1981.
11. Other methods of enzymatically incorporate biotin with DNA. Nucl. Acids Res. 13:45-56, 1985.
12. Photobiotin: a reagent that chemically links biotin to DNA by a reaction involving light. Nucl. Acids Res. 13:745-761, 1985.
13. Fusion protein with phage protein and other proteins. Science 228:1315-1317, 1985.
14. Chemically binding proteins to DNA. Nucl. Acids Res. 12:3435-3444, 1984.
15. Chemical coupling (proteins to peptides, proteins, spores or phages to probes; and other molecules):
    a. Diazonium.
       Nature 250:587-588, 1974.
       J Med. Chem 17:1304-1307, 1974.
    b. Acylation with activated carboxyl groups.
       Science 209:295-296, 1980.
       Science 215:1511-1513, 1982.
       Science 220:613-615, 1983.
    c. Using isothiocyante and bromacetamide.
       Anal. Biochem. 142:68-78, 1984.
    d. Other chemical coupling:
       Meth. Enzymol. 70:85-109, 1980.
       Meth. Enzymol. 70:151-159, 1980.

EXAMPLE 1

Southern Blottinq (a detailed example)

Restricted DNA is loaded on an 0.8% agarose gel in Tris Acetate Buffer and run at 40 volt overnight. The gel is stained with ethidium bromide and photographed. The gel is then treated twice in 0.25 HCl for 15 minutes each time at room temperature followed by two base treatments at room temperature in 0.5 M NaOH, 1.5 NaCl (15 minutes each) and two neutralization washes in 1 M ammonium acetate pH7.0 for 30 minutes each. The gel is then wick blotted (as described in Maniatis et al, pgs. 382-389) in 1 M ammonium acetate. Following blotting onto nitrocellulose the nitrocellulose blot is baked at 80° C. for 30 minutes under vacuum to bind the DNA to the nitrocellulose.

Preparation of Lambda Arms

Charon 35 BamHl arms were used. Charon 35 is a lambda phage Gene 26:171-179, 1983.) This phage was isolated (Maniatis et al, Molecular Cloning, A Laboratory Manual, Cold Spring Harbor Laboratory, (1982) pp. 80-82), and Charon DNA was isolated (Maniatis, p. 85). Vector DNA was restricted with BamHl restriction endonuclease, according to manufacturer's instructions, in 10 mM Tris HCl pH 7.5, 10 mM MgSO$_4$, 50 mM NaCl, 1 mM dithiothreitol (Maniatis, p. 453.) Arms of Charon 35 were isolated and separated from the stuffer fragments (Maniatis, pp. 75-277.)

Plasmid Preparation

The following plasmids were used in the construction of two phagemids as examples of phagemids capable of enabling bacterial cells to produce signals and selectively grow in accordance with the present invention:

(1) pJE202 (obtained from the Agaron Institute (Cell 32:773-781, 1983) contains the ampicillin-resistance gene, the luciferase operon (light production capabilities), the pBR322 origin of replication and related pBR322 sequences; and (2) pYAHB-cenIII (obtained from John Rossi, Beckman Research Institute of the City of Hope) contains an intact beta-galactosidase Z gene, ampicillin-resistance gene, pBR322 origin of replication and a yeast centromere.

Both plasmids were restricted with BamHl (according to manufacturer's instructions) and terminality of restriction was tested by running some of the cut plasmids on gels along with uncut controls. There is one BamHl site in each of these plasmids. The plasmids were extracted with phenol and chloroform:isoamyl alcohol (Maniatis et al, p. 438), precipitated with ethanol, and resuspended in small volume of TE buffer (Maniatis. p. 448).

Construction of Phagemids

A 2.5-microliter ligation reaction (for each plasmid) was done with 300 ng of BamHl-cut Charon 35 arms, 100 ng of BamHl-cut plasmid in 25 mM tris pH 7.8, 10 mM MgCl$_2$, 2 mM DTT (dithiothreitol), 0.4 mM ATP (adenosine triphosphate) with ligase enzyme to 0.1 units. This reaction was incubated overnight at 15° C. Packaging extract (obtained frozen from commerical source) was added to each ligation reaction. The thawing packaging extracts and ligated DNAs were (comprised of plasmid and phage arms from above) were incubated together for 60 minutes at room temperature. Following this incubation period, the packaged phagemid and other side products were diluted in SM media (Maniatis et al, p. 70) and a few drops of chloroform were added to prevent contaminating bacterial growth in this phage preparation.

Phagemid Purification

Phagemids were transfected into a JM109 λ Cl strain and selected on LB ampicillin plates with IPTG and Xgal for the Beta-galactosidase gene containing phagemid or, ampicillin LB plates (Maniatis et al, p. 71, 68, 70) for the luciferase-operon-containing phagemid and incubated at 30° overnight. Subsequent cultures were grown at 30° C. in LB media to an OD=0.5 at 660 nm. The JM109 λ Cl/λ JE (ATCC #67127) and JM109 (λ Cl/λ YAB (ATCC #67128) are on deposit in the ATCC. The cultures we induce (Maniatis, p. 78) by raising the temperature of the cultures to 45° C. for 30 minutes. This inactivates the λ repressor gene of the λ Cl$_{857}$ S7 lysogen which results in both the phagemid and formerly lysogenic phages being packaged, and the bacterial cells lysed. The resultant phage are diluted (Maniatis, p. 64) and a portion of the diluted phage are added to an excess of nonlysogenic bacteria. The bacteria are transfected by the phage at 37° C. for 10 minutes. The bacterial cell culture is plating and phagemid plaques were grown at 37° overnight and picked. Note that λ YAB, containing the galactosidase gene, can be seen in plaque form (blue plaques are formed in the presence of IPTG and Xgal). λ JE can not be distinguished in plaque form.

Blue λ YAB plaques were isolated, and diluted phage from these plaques was replated and single plaques from these plates were isolated followed by repeated dilution plating and reisolation from a single plague three times to ensure phagemid purity. The purified λ YAB phagemid was tested by transfection into the JM109 λ lysogen to ensure the intactness of the amplicillin gene and the plasmid origin of replication. A similar purification scheme was used for λ JE phagmid but testing of the phagemid had to be done at each cycle of the phage purification, using lysogenic JM109 to ensure the intactness of the luciferase operon (light production capabilities), the ampicillin resistance gene, and plasmid origin of replication.

Larger batches of phagemid were prepared (*Maniatis et al*, p. 65, 77-78, 80-82.) Phage preparations were dialyzed against SM and a few drops of chloroform were added. Gelatin was omitted from the phage preparations.

Biotinylating The Phage 5 mg of N-hydroxysuccinimido biotin (NHB) (from Sigma) was dissolved in 250 microliters of dimethyl formamide (sol. 1). 12.5 microliters of this solution was added to 237.5 microliters of dimethyl formamide (sol. 2). 100 microliters of phagemid stock $10^9$ pfu (plaque-forming units)/ml was diluted into 900 microliters of biotin buffer (7.5 mM $PO_4$ pH 7.2, 7.2 mM NaCl), with 20 mM $MgCl_2$ added to stabilize the phagemids. Solution 2 was vortexed while 750 microliters of distilled water was added drop by drop. The 1-ml phage solution was added immediately to the diluted solution 2, and incubated at 37° for 2 hours.

This results in phagemid biotinylation in which 50% of the phage are viable. This preparation was spun-dialyzed (Maniatis et al, pp. 466-467, on a 10-ml scale) in Sephadex G50-80, (hydrated in SM buffer without gelatin) (Maniatis, p. 70) in a clinical centrifuge, set at 3, for two min. The spin-dialysis removes unreacted NHB.

Coupling To Avidin

The biotinylated phagemid is added a drop at a time to a solution of streptavidin (in 10,000×molar excess) in SM, with gentle mixing. This solution was incubated for 10 minutes at room temperature, followed by two more spin-dialysis steps using standard SM buffer (containing gelatin) and resin as described above to eliminate unbound avidin.

Biotinylated DNA Hybridization

The DNA probe-biotin complex is hybridized to the complementary DNA sequence on the Southern blot under the conditions described in *Maniatis et al*, pgs. 382-389, except that the incubation is at 60°, and biotinylated DNA probe is employed in place of the radioactively labelled probe. After the high-stringency blot washes described in *Maniatis et al* at pp. 382-389, the blot is rinsed in SM buffer.

Phagemid Complex-Probe-Target Coupling

The Southern blot is prehybridized in SM with 1% BSA for 30 minutes at 37° C. Phagemids with attached biotin-avidin complex are added to the prehybridized Southern blot in SM 1% BSA. The reaction between avidin-phagemid complex and biotin-probe-target complex takes place for 60 min. at 37° C. The Southern blot is then washed six times for 5 minutes each in SM, 1% BSA, 0.01% tween 20 at room temperature to remove the non-specifically bound phagemid-biotin-avidin complex.

Signal Amplification And Detection

Bacteria (lysogens) are added and filters are transferred to ampicillin plates (with IPTG and Xgal for λ YAB phagemids). Colonies are grown at 30° overnight; then they are examined for blue colonies or light-producting colonies.

Some bacterial strains which may be employed include:

JM3 F′, met⁻ arg E⁻, Δlac-pro, B1⁻, Su III (tyr)

JM109 recA$^1$, Δlacpro,end Al,gyrA96,thi-1, hsdR17,SupE44, relAl,F′, traD36,proAB,-lacΔm15,lacI$^q$ JM103 Δlacpro,thi,strA,SupE,endA,sbcB,hsdR−,F′,-tra D36, proAB,lacI$^q$,lac ΔM15

DH-1 F′,recAl,endAl,gyrA96,thi-1,hsdR17($r_k^-$,$m_k^+$),SupE44,recAl, λ−

CES200 F′,thr-l,leuB6,proA2,sbcB15,his-4,recB21-,recC22, argE3,thi-1,ara14,lacYl,galK2,xyl-5,mtl-1,rpsL31,tsx33, λ-,hsd(r-,m+),thr::Tm10(+C+R). Lambda lysogens of JM109 and JM3 have generally been employed for colony production from the presently described phagemids.

Preparation of Lysogens From λ CI$_{857}$ S7 Phage

Take a bacterial culture grown on LB maltose overnight and pellet the bacterial suspension at 7000 g for 10 min. Resuspend the bacterial pellet in 0.4 volumes of SM. Add a slight excess (over bacterial count) of λ CI$_{857}$ S7 phage in SM to 200 ul of bacterial cells; incubate 10 min at 32° C.; plate the bacteria on LB medium with 10 mM $MgSO_4$. Pick individual colonies that grow overnight; dilute them and replate overnight. Select a colony from each plate derived from different colonies. Put these colonies on two plates; put one plate at 42° C. and one at 30° C. overnight.

Lambda lysogens of this temperature-sensitive phage will not allow colony formation at 42° C. Select colonies that grow at 30° C. but not at 42° C. Test those colonies with my phagemids. They should be able to product ampicillin-resistant colonies and either color (the λ YAB) or light (the λ JE). If not, they are not the proper lysogenic strain. Note that testing is done by growing these bacteria at 30° C. in maltose-magnesium-containing LB medium (see Maniatis'Cloning Manual) and going through the same protocol as used with the λ CI$_{857}$S7 phage, but plating on ampicillin-containing LB plates at 30° C. overnight.

EXAMPLE 2

Probe directly coupled to spore surface (this is a very direct approach in which the probe-modified spore undergoes binding just as a probe would.) This method eliminates the need for a transducing phagemid and eliminates many steps by directly coupling probe and spore. The nonspecifically bound spores would be removed after probe hybridization and the spores would grow out as bacterial colonies with any of a number of secondary signal mechanisms (light, color, or even just the presence of a visible colony).

In the preferred embodiment spores have been isolated which are capable of surviving DNA Southern blotting conditions, even the most severe hybridization done at 65° C. in 0.5 M $PO_4$, 7% sodium dodecyl sulfate overnight. Bacterial spores are linked chemically to a DNA probe (see references 15). Then the spore-probe combination is treated as though it were a standard DNA probe in a Southern blot hybridization but with bacteria added to the prehybridization and hybridization steps to limit nonspecific binding of the spore to the membrane. Following hybridization stingency washes are done in an ultrasonic cleaner with its ultrasonic vibration output regulated to a fraction of its full power setting. The exact setting will depend on the probe and spore used and must be determined empirically. After five to six washes (five minutes each) the membrane with remaining specifically bound spores is placed on agar nutrient broth medium (Difco 0001) plus indicator dye and incubated at the appropriate temperature (55° C. for Bacillus Stearothermophilus) overnight. Bacterial colonies will grow up over specific target sites and will be readily visible due to their color uptake against the white substratum.

In another version of the concept phages, phagemids, viruses, or prions could be used in a shortened protocol provided that they are capable of surviving conditions used to bind probe to target and remove nonspecifically bound probe. One would chemically couple the phage to the probe or use a phage with the probe existing as a fusion protein on its surface. Following probe-phage-binding and removal of nonspecifically bound probe-phage the bacteria would be added without all the intermediary steps set forth in the example.

I claim:

1. A process for detecting the presence of a target molecule which comprises:
   binding said target molecule to a substrate,
   combining said target molecule with a target molecule specific probe to form a target molecule-probe combination,
      said probe bearing one of a pair of moieties which bind inter se,
   binding said target molecule probe combination to a phagemid bearing the other one of said pair of moieties which bind inter se,
      the plasmid portion of said phagemid containing a signal encoding DNA
   transfecting said phagemid into a lysogenic cell effective to express the signal encoding DNA present in the plasmid portion of said phagemid
   replicating said transfected cell
   detecting the expression of said signal encoding DNA by the replicated cells
   and relating the detected signal to the presence of the target molecule.

2. A process as defined by claim 1 in which the lysogenic cell is a lac$^-$ λ lysogen.

3. A process as defined by claim 1 in which said pair of moieties that bind inter se consists of streptavidin and biotin.

4. A process as defined by claim 1 or claim 16 in which the target molecule is a DNA molecule, an RNA molecule, a peptide molecule or a lipoprotein molecule.

5. A process for detecting the presence of a target molecule which comprises:
   binding said target molecule to a substrate,
   combining said target molecule with a target molecule specific probe to form a target molecule-probe complex,
      said probe bearing one of a pair of moieties which bind inter se,
   binding said target molecule probe complex to a phagemid bearing the other one of said pair of moieties which bind inter se,
      the plasmid portion of said phagemid containing a single encoding DNA comprising a luciferase signal sequence,
   transfecting said phagemid into a lysogenic cell effective to express the signal encoding DNA present in the plasmid portion of said phagemid,
   replicating said transfected cell,
   detecting the expression of said signal encoding DNA by the replicated cells, and relating the detected signal to the presence of the target molecule.

6. A process for detecting the presence of a target molecule which comprises:
   binding said target molecule to a substrate,
   combining said target molecule with a target molecule specific probe to form a target molecule-probe complex,
      said probe bearing one of a pair of moieties which bind inter se,
   binding said target molecule probe complex to a phagemid bearing the other one of said pair of moieties which bind inter se,
      the plasmid portion of said phagemid containing a single encoding DNA comprising a luciferase or β-galactosidase signal sequence,
   transfecting said phagemid into a lysogenic cell effective to express the signal encoding DNA present in the plasmid portion of said phagemid,
   replicating said transfected cell,
   detecting the expression of said signal encoding DNA by the replicated cells, and relating the detected signal to the presence of the target molecule.

* * * * *